United States Patent
Schmidt et al.

(10) Patent No.: US 9,267,891 B2
(45) Date of Patent: Feb. 23, 2016

(54) MULTIPLEX FLUORESCENT PARTICLE DETECTION USING SPATIALLY DISTRIBUTED EXCITATION

(75) Inventors: Holger Schmidt, Capitola, CA (US); Aaron Roe Hawkins, Provo, UT (US)

(73) Assignees: The Regents of the University of California, Oakland, CA (US); Brigham Young University, Provo, UT (US)

(*) Notice: Subject to any disclaimer, the term of this patent is extended or adjusted under 35 U.S.C. 154(b) by 196 days.

(21) Appl. No.: 14/124,589

(22) PCT Filed: Jun. 4, 2012

(86) PCT No.: PCT/US2012/040750
§ 371 (c)(1),
(2), (4) Date: Apr. 10, 2014

(87) PCT Pub. No.: WO2012/170352
PCT Pub. Date: Dec. 13, 2012

(65) Prior Publication Data
US 2014/0313510 A1    Oct. 23, 2014

Related U.S. Application Data

(60) Provisional application No. 61/493,701, filed on Jun. 6, 2011.

(51) Int. Cl.
*G01N 21/64* (2006.01)
*G01N 21/49* (2006.01)
(Continued)

(52) U.S. Cl.
CPC ........ *G01N 21/6486* (2013.01); *G01B 9/02041* (2013.01); *G01N 15/1436* (2013.01);
(Continued)

(58) Field of Classification Search
CPC . G01N 21/6486; G01N 21/532; G01N 21/53; G01N 21/49; G01N 15/1434; G01N 2015/144; G01N 2015/1447; G01N 21/145; G01N 15/1436; G01N 21/05; G01N 21/645; G01N 15/1459; G01N 15/1484; G01N 2015/1006; G01N 2021/0346; G01N 2021/058
See application file for complete search history.

(56) References Cited

U.S. PATENT DOCUMENTS 4,324,492 A * 4/1982 Drenckhan ........ G02B 6/12004
356/481
7,127,146 B2   10/2006 Schmidt et al.
(Continued)

OTHER PUBLICATIONS

Chen et al., "Scattering-Based Cytometric Detection Using Integrated Arrayed Waveguides with Microfluidics", IEEE Photonics Technology Letters, Mar. 15, 2007, 19(6) 441-443.
(Continued)

*Primary Examiner* — Michael P Lapage
(74) *Attorney, Agent, or Firm* — Baker & Hostetler LLP (57) ABSTRACT

A chip-scale optical approach to performing multi-target detection is based on molecular biosensing using fiber-optic based fluorescence or light scattering detection in liquid-core waveguides. Multiplexing methods are capable of registering individual nucleic acids and other optically responsive particles, and are ideal for amplification-free detection in combination with the single molecule sensitivity of optofluidic chips. This approach overcomes a critical barrier to introducing a new integrated technology for amplification-free molecular diagnostic detection. Specific examples of liquid-core optical waveguides and multi-mode interferometers are described; however, they can be implemented in a number of different ways as long as a series of excitation spots is created whose spacing varies with the excitation wavelength.

17 Claims, 6 Drawing Sheets

(51) Int. Cl.
G01N 15/14 (2006.01)
G01N 21/05 (2006.01)
G01N 21/53 (2006.01)
G01B 9/02 (2006.01)
G01N 15/10 (2006.01)
G01N 21/03 (2006.01)

(52) U.S. Cl.
CPC ........ *G01N15/1459* (2013.01); *G01N 15/1484* (2013.01); *G01N 21/05* (2013.01); *G01N 21/49* (2013.01); *G01N 21/53* (2013.01); *G01N 21/645* (2013.01); *G01N 2015/1006* (2013.01); *G01N 2015/145* (2013.01); *G01N 2021/0346* (2013.01); *G01N 2021/058* (2013.01)

(56) References Cited

U.S. PATENT DOCUMENTS

| 7,149,396 | B2 | 12/2006 | Schmidt et al. | |
|---|---|---|---|---|
| 7,248,771 | B2 | 7/2007 | Schmidt et al. | |
| 7,391,949 | B2 | 6/2008 | Schmidt et al. | |
| 7,444,053 | B2 | 10/2008 | Schmidt et al. | |
| 7,995,890 | B2 | 8/2011 | Schmidt et al. | |
| 8,005,332 | B2 | 8/2011 | Schmidt et al. | |
| 8,385,693 | B2 | 2/2013 | Schmidt et al. | |
| 2003/0072521 | A1 | 4/2003 | Mukai | |
| 2008/0278710 | A1 | 11/2008 | Schmidt et al. | |
| 2009/0175586 | A1 | 7/2009 | Schmidt et al. | |
| 2010/0051788 | A1* | 3/2010 | Klunder | G01N 21/6452 250/216 |
| 2010/0271634 | A1* | 10/2010 | Dominguez Horna | G01N 21/45 356/477 |
| 2011/0169944 | A1* | 7/2011 | Zhao | G01N 21/8806 348/126 |
| 2012/0019833 | A1* | 1/2012 | Ymeti | G01N 21/45 356/477 |
| 2012/0214707 | A1* | 8/2012 | Ymeti | G01N 21/45 506/9 |

OTHER PUBLICATIONS

Hamamoto et al., "First demonstration of novel active multi-mode interferometer (MMI) LOs integrated with 1st order-mode permitted waveguides", IEICE Electronics Express, Jul. 10, 2005, 2(13) 399-403.
International Patent Application No. PCT/US2012/040750: International Search Report and Written Opinion dated Nov. 23, 2012, 10 pages.
Sanders et al.; "Chip-based microsystems for genomic and proteomic analysis"; Trends in Anal. Chem. vol. 19 No. 6; 2000; p. 364-378.
Heller; "DNA microarray technology: Devices, systems, and applications", Ann. Rev. Biomed. Eng. 4; 2002; p. 129-153.
Chamberlain et al.; "Deletion screening of the Duchenne muscular dystrophy locus via multiplex DNA amplification"; Nucleic Acids Research; vol. 16 No. 23; 1988; p. 11141-11156.
Hayden et al.; "Multiplex-ready PCR: a new method for multiplexed SSR and SNP genotyping"; BMC Genomics 9; Feb. 2008; 12 pages.
MacBeath et al.; "Printing Proteins as Microarrays for High-Throughput Function Determination"; Science vol. 289; 2000; p. 1760-1763.
Stoevesandt et al.; "Protein microarrays: high-throughput tools for proteomics"; Expert Reviews Proteomics 6; 2009; p. 145-157.
Rabkin et al.; "Interassay correlation of human herpesvirus 8 serologic tests", J. Infect. Dis. 178; 1998; p. 304-309.
Ling et al.; "Multiplexing molecular diagnostics and immunoassays using emerging microarray technologies"; Expert Review Mol. Diagnostics 7; 2007; p. 87-98.
Watzinger et al.; "Detection and monitoring of virus infections by real-time PCR"; Molecular Aspects of Medicine 27; 2006; p. 254-298.
Nitsche et al.; "Different real-time PCR formats compared for the quantitative detection of human cytomegalovirus DNA"; Clin. Chem. 45; 1999; p. 1932-1937.
Vasioukhin et al.; "Point mutations of the N-ras gene in the blood plasma DNA of patients with myelodysplastic syndrome or acute myelogenous leukaemia"; British Journal of Haematology 86; 1994; p. 774-779.
Anker et al.; "K-ras mtuations are found in DNA extracted from the plasma of patients with colorectal cancer"; Gastroenterology, vol. 112 No. 4; Apr. 1997; p. 1114-1120.
Swarup et al.; "Circulating (Cell-free) nucleic acids—a promising, non-invasive tool for early detection of several human cancers"; FEBS Letters 581; 2007; p. 795-799.
Fleischhacker et al.; "Circulating nucleic acids (CNAs) and cancer—a survey"; Biochim. Biophys. Acta 1775; 2007; p. 181-232.
Chiminqgi et al.; "Specific real-time PCR vs. fluorescent dyes for serum-free DNA quantification"; Clin. Chem. Lab. Med. 45; 2007; p. 993-995.
Piatak et al.; "High levels of HIV-1 in plasma during all stages of infection determined by competitive PCR"; Science 259; 1993; p. 1749-1754.
Inoue et al.; "WT1 as a new prognostic factor and a new marker for the detection of minimal residual disease in acute leukemia"; Blood vol. 84 No. 9; 1994; p. 3071-3079.
Taberlet et al.; "Reliable genotyping of samples with very low DNA quantities using PCR"; Nucl. Acids Res. vol. 24 No. 16; 1996; p. 3189-3194.
Lagally et al.; "Fully integrated PCR-capillary electrophoresis microsystem for DNA analysis"; Lab Chip 1; 2001; p. 102-107.
Liu et al.; "Integrated DNA purification, PCR, sample cleanup, and capillary electrophoresis microchip for forensic human identification"; Lab Chip 11; 2011; p. 1041-1048.
Chiu et al.; "Diagnosis of a critical respiratory illness caused by human metapneumovirus by use of a pan-virus microarray"; J Clin Microbial. vol. 45 No. 7; 2007; p. 2340-2343.
Chiu et al.; "Microarray detection of human parainfluenzavirus 4 infection associated with respiratory failure in an immunocompetent adult"; Clin Infect Dis. 43; 2006; p. e71-76.
Tang et al.; "Metagenomics for the discovery of novel human viruses"; Future Microbial. 5; 2010; p. 177-189.
Yin et al.; "Integrated optical waveguides with liquid cores"; Applied Physics Letters; vol. 85 No. 16; Oct. 2004; p. 3477-3479.
Schmidt et al.; "Optofluidic waveguides: I. Concepts and implementations", Microfluid and Nanofluidics vol. 4; 2008; 26 pages.
Hawkins et al.; "Optofluidic waveguides: II. Fabrication and structures"; Invited review, Microfluid and Nanofluidics vol. 4; 2007; 34 pages.
Barber et al.; "Fabrication of Hollow Waveguides with Sacrificial Aluminum Cores"; IEEE Photonics Technology Letters; vol. 17; Feb. 2005; p. 363-365.
Barber et al.; "Integrated Hollow Waveguides with Arch-shaped Cores"; IEEE Photonics Technology Letters; vol. 18; Jan. 2006; p. 28-30.
Hubbard et al.; "Structural models and design rules for on-chip micro-channels with sacrificial-cores"; Journal of Micromechanics and Microengineering 15; 2005; p. 720-727.
Lunt et al.; "Improving solid to hollow core transmission for integrated ARROW waveguides"; Optics Express vol. 16 No. 25; 2008; p. 20981-20986.
Zhao et al.; "Hollow Waveguides with Low Intrinsic Photoluminescence Fabricated with Ta20s and Si02 Rims,"; Applied Physics Letters vol. 98; 2011; 3 pages.
Yin et al.; "Highly efficient fluorescence detection in picoliter volume liquid-core waveguides"; Applied Physics Letter vol. 87; 2005; 3 pages.
Yin et al.; "Microphotonic control of single molecule fluorescence correlation spectroscopy using planar optofluidics"; Optics Express vol. 15 No. 12; 2007; p. 7290-7295.
Yin et al.; "Single-molecule detection sensitivity using planar integrated optics on a chip"; Optics Letter vol. 31 No. 4; Jul. 2006; p. 2136-2138.
Kuhn et al.; "Loss-based optical trap for on-chip particle analysis"; Lab on Chip 9; 2009; 11 pages.

(56) References Cited

OTHER PUBLICATIONS

Measor et al.; "Multi-mode mitigation in an optofluidic chip for particle manipulation and sensing"; Optics Express vol. 17 No. 26; 2009; p. 24342-24348.

Chen et al.; "Dual-color fluorescence cross-correlation spectroscopy on a planar optofluidic chip"; Lab on Chip 11; 2011; p. 1502-1506.

Yin et al.; "Planar optofluidic chip for single particle detection, manipulation, and analysis", Lab Chip 7; 2007; p. 1171-1175.

Rudenko et al.; "Ultrasensitive QB Phage Analysis Using Fluorescence Correlation Spectroscopy on an Optofluidic Chip"; Biosensors and Bioelectronics vol. 24; 2009; 14 pages.

Tyagi et al.; "Molecular beacons: probes that fluoresce upon hybridization"; Nature Biotechnol. vol. 14; 1996; p. 303-308.

Drake et al.; "Molecular beacon DNA probes and their bioanalytical applications"; Applied Spectroscopy vol. 58 No. 9; 2004; p. 269-280.

Bonnet et al.; "Thermodynamic basis of the enhanced specificity of structured DNA probes"; PNAS vol. 96; 1999; p. 6171-6176.

Sinsimer et al.; "Use of a multiplex molecular beacon platform for rapid detection of methicillin and vancomycin resistance in *Staphylococcus aureus*"; J. Clinical Microbiology vol. 43 No. 9; 2005; p. 4585-4591.

Soldano et al.; "Optical multi-mode interference devices based on self-imaging: Principles and applications"; J. Lightw. Tech. vol. 13 No. 4; 1995; p. 615-627.

Li et al.; "1×2 optical waveguide filters based on multimode interference for 1.3 and 1.55mm operation"; Opt. Eng. 41; 2002; p. 723-727.

Khalil et al.; "Two-dimensional multimode interference in integrated optical structures"; Journal of Optics A.; vol. 6; 2004; p. 137-145.

Lien et al.; "High sensitivity cytometric detection using fluidic-photonic integrated circuits with array waveguides"; IEEE Journal Selective Topics Qu. Elec. vol. 11; 2005; p. 827-834.

Godin et al.; "Microfluidics and photonics for bio-system-on-a-chip: A review of advancements in technology towards a microfluidic flow cytometry chip"; Journal of Biophotonics 1 No. 5; 2008; p. 355-376.

\* cited by examiner

$F(t)=S(t)*S(t-\Delta t)*\ldots*S(t-(k-1)\Delta t)$

MULTIPLEX FLUORESCENT PARTICLE DETECTION USING SPATIALLY DISTRIBUTED EXCITATION

CROSS-REFERENCE TO RELATED APPLICATIONS

This application is the National Stage of International Application No. PCT/US2012/040750, filed Jun. 4, 2012, which claims the benefit of U.S. Provisional Application No. 61/493,701, filed Jun. 6, 2011, the disclosures of which are incorporated herein by reference in their entireties.

TECHNICAL FIELD

This application describes the application of spatially distributed, interferometric excitation using integrated interferometer structures for ultrasensitive particle detection.

BACKGROUND

The inventive subject matter described herein is related to the subject matter described in the following U.S. Patents and Published Patent Applications invented by Drs. Holger Schmidt and Aaron Hawkins. These patent documents enable novel devices and methods in the fields of integrated optofluidics (e.g., based on micron-scale liquid-core optical waveguides where light and fluids are guided on a chip, enabling novel methods for on-chip detection and manipulation of single particles for a new class of portable biomedical analytic instruments); nanopores in optofluidic devices (e.g., nanoscopic openings in membranes are used as electrical single molecule detectors using optofluidic devices to combine both electrical and optical detection on a single chip); and single-photon nonlinear optics (e.g., atomic vapor cells on an integrated optical waveguide chip enable the guiding of light through small volumes of rubidium vapor, which in turn enables the study of quantum interference effects on a chip, including induced transparency, slow light and single photon nonlinearities):

Publication Number: U.S. Pat. No. 8,005,332B2
Title: Integrated optical vapor cell apparatus for precision spectroscopy
Publication Date: 2011 Aug. 23
Publication Number: U.S. Pat. No. 7,995,890B2
Title: Device for light-based particle manipulation on waveguides
Publication Date: 2011 Aug. 9
Publication Number: U.S. Pat. No. 7,444,053B2
Title: Integrated electrical and optical sensor for biomolecule analysis with single molecule sensitivity
Publication Date: 2008 Oct. 28
Publication Number: U.S. Pat. No. 7,391,949B2
Title: Low loss hollow core optical waveguide
Publication Date: 2008 Jun. 24
Publication Number: U.S. Pat. No. 7,248,771B2
Title: Integrated sensor with electrical and optical single molecule sensitivity
Publication Date: 2007 Jul. 24
Publication Number: U.S. Pat. No. 7,149,396B2
Title: Apparatus for optical measurements on low-index non-solid materials based on arrow waveguides
Publication Date: 2006 Dec. 12
Publication Number: U.S. Pat. No. 7,127,146B2
Title: Apparatus for optical measurements on low-index non-solid materials based on arrow waveguides
Publication Date: 2006 Oct. 24
Publication Number: US20110253295A1
Title: Integrated Optical Vapor Cell Apparatus for Precision Spectroscopy
Publication Date: 2011 Oct. 20
Publication Number: US20090175586A1
Title: DEVICE FOR LIGHT-BASED PARTICLE MANIPULATION ON WAVEGUIDES
Publication Date: 2009 Jul. 9
Publication Number: US20080278710A1
Title: Integrated Optical Vapor Cell Apparatus for Precision Spectroscopy
Publication Date: 2008 Nov. 13
Publication Number: US20070122097A1
Title: Low loss hollow core optical waveguide
Publication Date: 2007 May 31
Publication Number: US20060251371A1
Title: Integrated electrical and optical sensor for biomolecule analysis with single molecule sensitivity
Publication Date: 2006 Nov. 9
Publication Number: US20060098927A1
Title: Integrated sensor with electrical and optical single molecule sensitivity
Application Date: 2005 Oct. 14
Publication Date: 2006 May 11
Publication Number: US20060008227A1
Title: Apparatus for optical measurements on low-index non-solid materials based on arrow waveguides
Publication Date: 2006 Jan. 12
Publication Number: US20040252957A1
Title: Apparatus for optical measurements on low-index non-solid materials based on arrow waveguides
Publication Date: 2004 Dec. 16

Figure 1A:
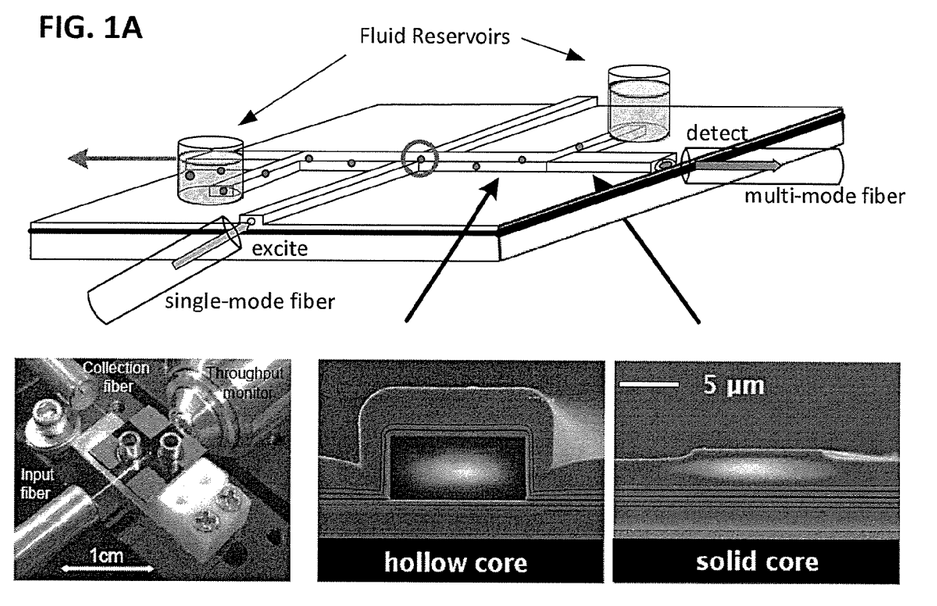
FIG. 1a shows an optofluidic chip, images of waveguide cross sections, and the chip under test.

FIG. 1a shows a planar optofluidic platform the inventors have developed for ultrasensitive fluorescence detection. (This platform is described in detail in the above-cited US patent documents.) Liquid-core antiresonant reflecting optical waveguides (ARROWS) with typical core dimensions of 5×12 μm (see SEM, bottom center, with super-imposed image of the guided mode) are interfaced with solid-core waveguides (see SEM in bottom right) at different points of the liquid core [26] (bracketed numerals refer to the literary references cited below). The devices are fabricated on a silicon chip using standard microfabrication techniques involving deposition of dielectric layers in combination with sacrificial layer etching [28-33]. Excitation light enters the liquid core through an orthogonally intersecting solid-core ARROW. Fluorescence from molecules in the core is collected perpendicularly in the chip plane and guided along the liquid-core channels [34]. This arrangement enables single particle sensitivity by creating femtoliter optical excitation volumes [35,36]. Fluidic reservoirs at the channel ends allow for channel filling and insertion of electrodes to induce electrokinetic particle movement. The photograph in the bottom left of FIG. 1 illustrates the optofluidic chip under test. This platform has successfully been used for fluorescence analysis of a variety of particles, including microbeads [37-39], single dye molecules [35,36], liposomes [40] and ribosomes, and virus capsids [41].

Figure 1B:
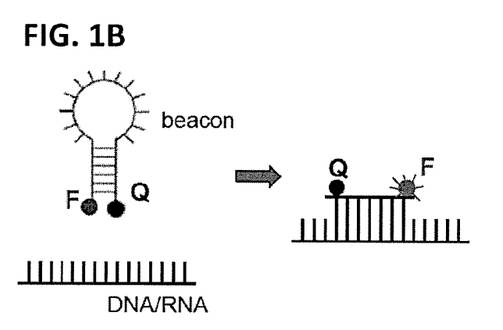
FIG. 1b depicts the principle of molecular beacon for detection.
Figure 1C:
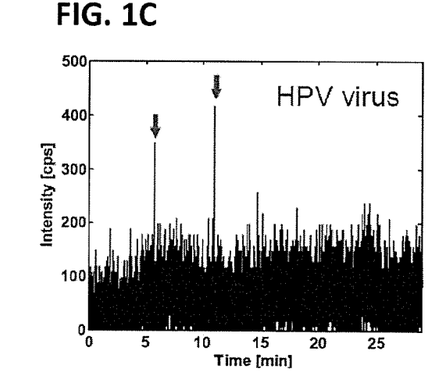
FIG. 1c shows an on-chip optical detection of single HPV viral DNAs using matching molecular beacon probes.

FIG. 1b shows the molecular beacon approach that can be used for specific detection of nucleic acids. Beacon detection is both highly sensitive and specific [42-44]. FIG. 1c shows the on-chip detection of single HPV-18 (human papillomavirus) DNA molecules as they flow by the excitation spot. This shows that amplification-free detection of pathogen nucleic acids is possible on a small optofluidic chip.

Integrated biosensing platforms are a topic of intense current research interest. With a wide range of biological targets (cells to molecular biomarkers), sensing mechanisms (optical, electrical, magnetic etc.), and deployment locations (clinical research labs to point-of-care), a unified description is virtually impossible. There is, however, widespread agreement over the fact that emerging molecular diagnostic instruments need to be compact, inexpensive, and simple in construction and use, while featuring high sensitivity and specificity. Simultaneous detection of multiple targets ("multiplexing") is a valuable feature of such platforms.

Multiplex detection has been applied to different diagnostic targets, including nucleic acids (e.g. DNA microarrays [1,2], multiplex polymerase chain reaction (PCR) [3,4]), proteins (protein microarrays [5,6]) and others (e.g. ELISAs (enzyme-linked immunosorbent assays [7,8]). Detection is typically accomplished using optical fluorescence which bears the potential of both spatial (multiple detection locations) and spectral (multiple wavelengths) multiplexing and possible combinations of both. PCR methods are excellent examples for the significance of multiplexing. They are the current gold standard for molecular diagnostics, and the underlying nucleic acid detection is ideally suited for next generation genome-based analysis with a broad range of applications, including pathogen detection [9-11], mutation analysis [12,13], cancer detection [14-16], disease monitoring [17,18], and forensic studies [19-21]. Commercially available kits (e.g. Qiagen) allow for up to ~16× multiplexing in 1000 parallel reactions, while research platforms such as the Virochip have demonstrated parallel amplification of up to 1,000 targets [22-24]. However, multiplex PCR is complex and slow [22] and requires a target amplification step with several drawbacks [10]. Therefore, an on-chip approach for molecular diagnostics that provides 10-100× target multiplexing without the need for target amplification is highly significant.

SUMMARY

The present disclosure describes a new chip-scale optical approach to performing multi-target detection. The described techniques are based on molecular biosensing using fiber-optic based fluorescence detection in liquid-core waveguides [25-27]. The novel multiplexing methods are capable of registering individual nucleic acids and are thus ideal for amplification-free detection in combination with the single molecule sensitivity of the optofluidic chips. Thus, this invention will overcome a critical barrier to introducing a new integrated technology for amplification-free molecular detection. While the ideas are described using the specific examples of liquid-core optical waveguides and multi-mode interferometers, they can be implemented in a number of different ways as long as a series of excitation spots is created whose spacing varies with the excitation wavelength.

According to the present invention, spatially distributed interferometric excitation is used in a diagnostic instrument. The method comprises creating a wavelength dependent excitation pattern in a multi-mode interferometer (MMI), causing a fluorescent particle to flow past the MMI so as to produce k fluorescence pulses at time steps $\Delta t$, detecting the k fluorescence pulses, and identifying the fluorescent particle based on a predefined algorithm. In an exemplary embodiment, the MMI comprises an optical waveguide supporting N waveguide modes that propagate in the optical waveguide with different wave vectors, or speeds, and the N modes comprise electric fields that interfere to create varying field patterns with k well-defined spots spaced by w/k at lengths $L_k = 3L_\pi/(4k)$, where $L_\pi$ is a characteristic length that depends on the MMI width w and scales inversely with wavelength $\lambda$. (See [46].)

In accordance with another aspect of the invention, spatial multiplexing is achieved by exciting a plurality of multi-mode interferometers in parallel. For example, at least first and second multi-mode interferometers may be employed to excite first and second channels, respectively, wherein each channel is excited with an MMI using the same wavelength but different MMI dimensions corresponding to different numbers of excitation spots such that particles flowing through the different channels produce fluorescence peaks at distinct time intervals.

In accordance with another aspect of the invention, spectral multiplexing is achieved by exciting the MMI with first and second excitation light colors, thereby producing different spot spacings and, thus, different correlation times $\Delta t(\lambda)$. In addition, a combination of spatial and spectral multiplexing may be performed.

Further aspects of the inventive subject matter are described below.

DETAILED DESCRIPTION OF ILLUSTRATIVE EMBODIMENTS

We will now explain our invention in sufficient detail to enable a person of ordinary skill in the field of integrated optics to make and use the invention without undue experimentation. The following description is not intended (nor would it be possible) to serve as an exhaustive discussion of every possible embodiment, application or method of manufacturing a device within the scope of our invention. It is sufficient, however, to enable the skilled artisan to practice our invention. We will focus our discussion on several important aspects of the inventive method for amplification-free detection of nucleic acids and other optically responsive particles on optofluidic chips. These aspects include (a) multiplex detection via spatially distributed interferometric excitation; (b) spatial multiplexing via multi-channel excitation; (c) spectral multiplexing via multi-wavelength excitation; and (d) combinatorial multiplexing via multi-channel, multi-wavelength excitation.

Multiplex Detection Via Spatially Distributed Interferometric Excitation

Figure 2A:
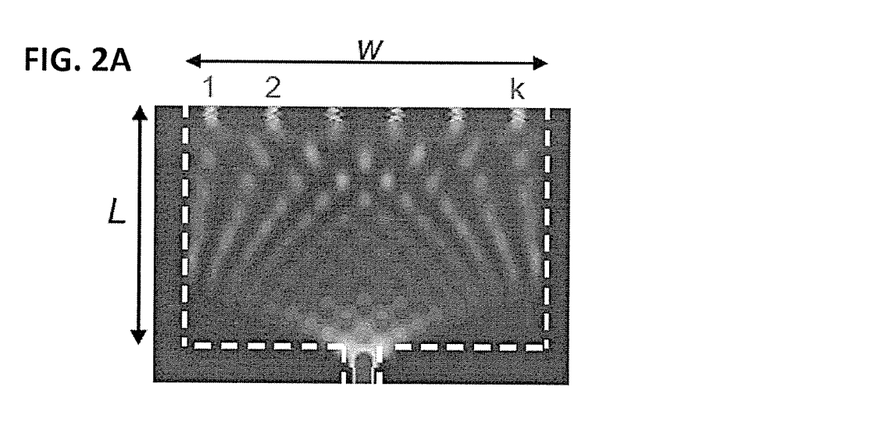
FIG. 2a shows light distribution in a multi-mode interferometer (MMI).

The ability to detect a sufficiently large number of targets (10-100) simultaneously is critical for a molecular diagnostic instrument. Here, we describe a novel fluorescence excitation method: spatially distributed interferometric excitation. This new concept is based on a multi-mode interferometer (MMI), an integrated optical structure that is well known in solid-state optoelectronics [46-48]. Briefly, a narrow waveguide supporting only a single transverse mode is expanded into a wide section that sustains N modes (FIG. 2a), where N is an integer greater than 1. These modes propagate with different wave vectors ("speeds") and their electric fields continuously interfere to create varying field patterns as seen in the figure. Specifically, patterns with k (where k is an integer) well-defined spots spaced by w/k are created at MMI lengths $L_k=3L_\pi \pi/(4k)$, where $L_\pi$ is a characteristic length that depends on the MMI width w and scales inversely with wavelength $\lambda$ [46]. Thus, we can create wavelength dependent excitation patterns that can then be used for signal processing algorithms similar to [49].

Figure 2B:
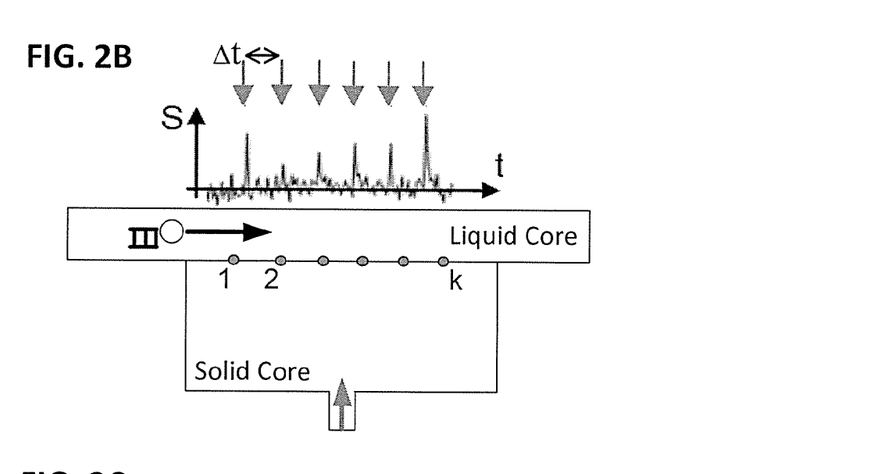
FIG. 2b shows MMI on ARROW chip for spatially distributed excitation and resulting fluorescence signal.

FIG. 2b shows the proposed implementation in the ARROW platform. As shown, what is required is a widening of the solid-core waveguide connecting to the liquid channel. This requires no additional fabrication steps, and even produces a waveguide with lower loss [26]. A fluorescent particle flowing past the MMI section will produce k fluorescence pulses at equal time steps $\Delta t$.

Figure 2C:
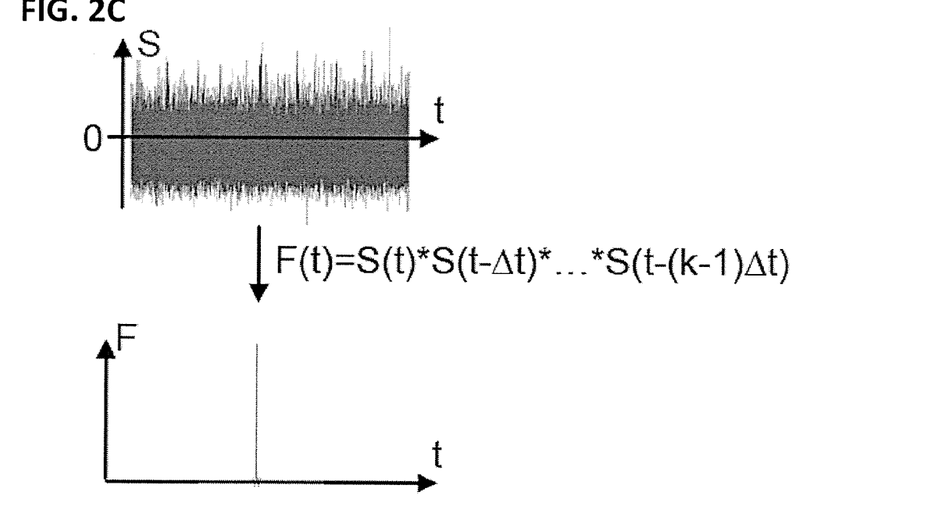
FIG. 2c shows a simulated detector signal with fluorescence from 8 excitation spots buried in background noise.

FIG. 2c shows such a simulated signal (k=8) completely buried within random background noise. As shown, the signal is retrieved and the particle is identified with high fidelity using a predefined algorithm that comprises creating a new signal F(t) from the measured detector signal S(t) in the following way: $F(t)=S(t)*S(t-\Delta t)* \ldots *S(t-(k-1)*\Delta t)$, where $\Delta t$ is the time it takes for the fluorescent or scattering particle to move from one of the excitation spots to the next. (See FIG. 2c, bottom and Lien [49-51]).

Spatial Multiplexing Via Multi-Channel Excitation

Figures 3A, 3B:
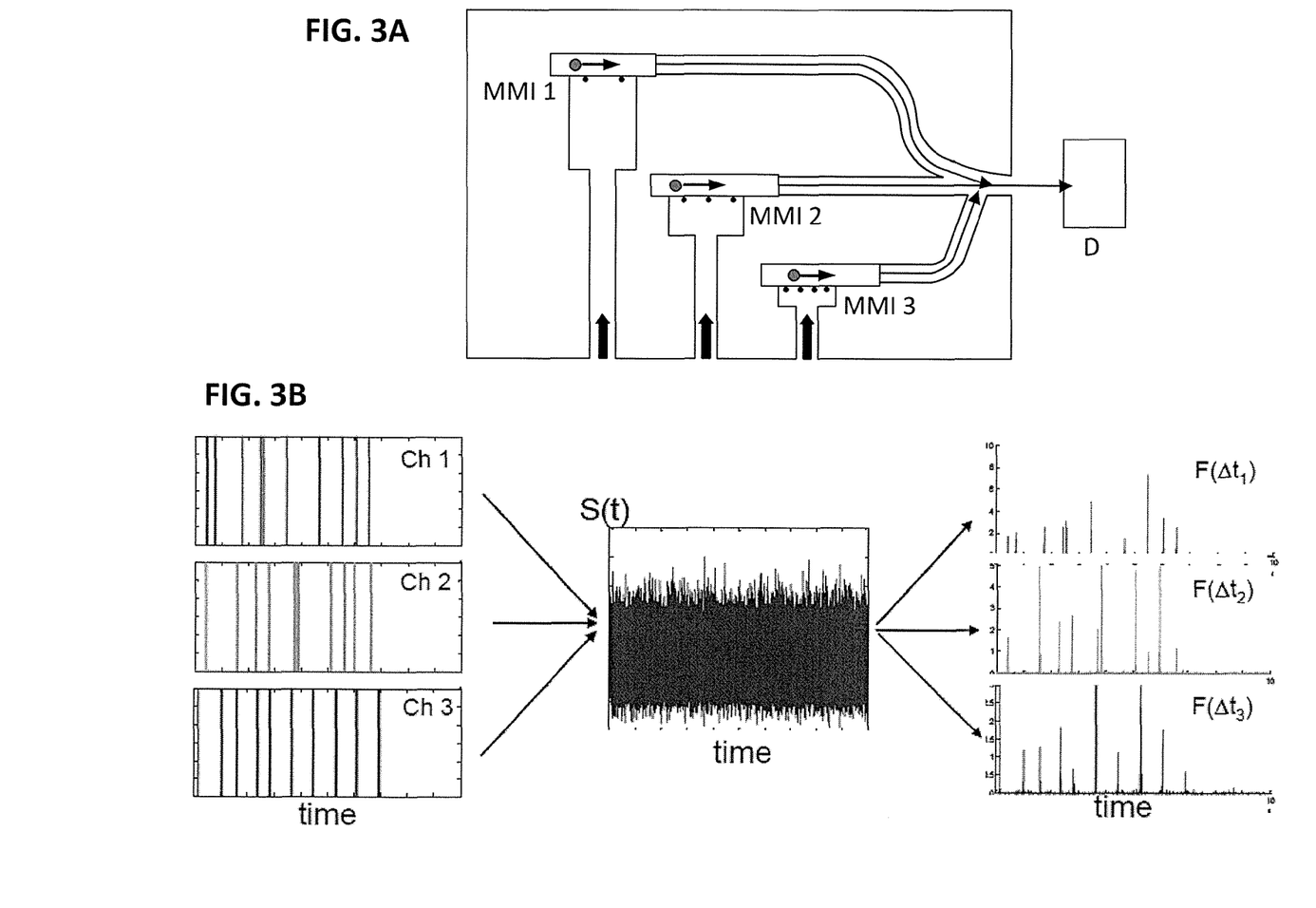
FIG. 3a depicts a sketch of three detection channels excited by MMIs of different lengths and thus differently spaced excitation spots, and depicts these channels being input to a detector (D). Detector D is also represented in FIGS. 4B and 5C.
FIG. 3b (left side): shows simulated fluorescence signal from 10 particles in each channel; (center): signal plus background noise recorded by single detector; and (right side): retrieved particles by analyzing signal three times with characteristic peak spacing $\alpha t_i$ for each channel.

The first way to use interferometric excitation for multiplexing will be to analyze multiple channels in parallel. An example with three parallel liquid waveguide channels is shown in FIG. 3a. (Note that the fluidic reservoirs and 1-3 waveguide splitter at the input side are not shown for clarity, but are fully compatible with chip dimensions and fabrication process.)

Each channel is excited with an MMI using the same wavelength but different MMI dimensions (widths $w_i$ and/or lengths Li) corresponding to different numbers of excitation spots (2, 3, 4 in the figure). Thus, particles flowing through the different channels will produce fluorescence peaks at distinct time intervals, specific to each channel. FIG. 3b illustrates how this concept will work in practice. On the left are simulated signals from 10 particles flowing through each channel. These will all hit the detector together with noise and background signal. In fact, the particles are not visible anymore in the simulated signal in the center. However, when this signal is processed with the three distinct delay times, all particles in all channels are recovered with high signal-to-noise ratio (right panels). This means that signal can be recorded simply and cheaply with a single detector, while particle detection and assignment to the channel of origin is done with a simple mathematical algorithm.

Spectral Multiplexing Via Multi-Wavelength Excitation

Figure 4A:
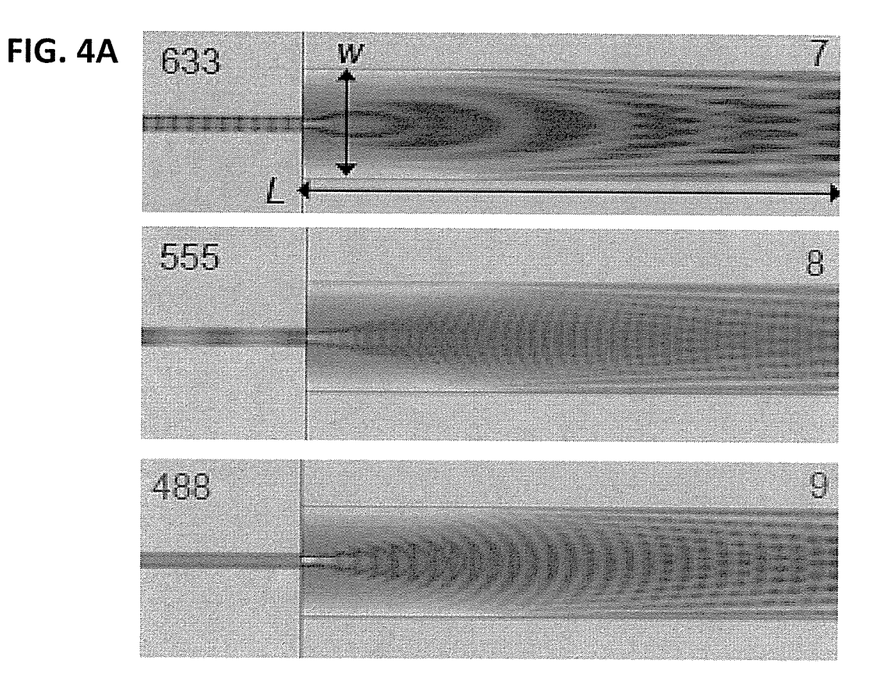
FIG. 4a depicts the mode simulations of 3 wavelengths producing 7, 8, and 9 excitation spots in a single MMI.

Spatial multiplexing could be accomplished in principle with k individual excitation waveguides, albeit at much higher losses and therefore reduced sensitivity. Spectral multiplexing, on the other hand, relies on the wavelength dependence of interference effects and can only be realized with an interferometric structure such as the MMI. The idea is illustrated in FIG. 4a. An MMI of a given length will produce different numbers of excitation spots for different wavelengths. As a result, different excitation colors will result in different spot spacings and, thus, different correlation times $\Delta t(\lambda)$. The dimensions (w, L) can be easily designed to coincide with the excitation wavelengths of different dyes. FIG. 4a shows the example of w=50 µm, L=875 µm producing 7, 8, and 9 spots for excitation of the common dyes Alexa 488, Alexa 555, and Alexa 647, respectively.

Figure 4B:
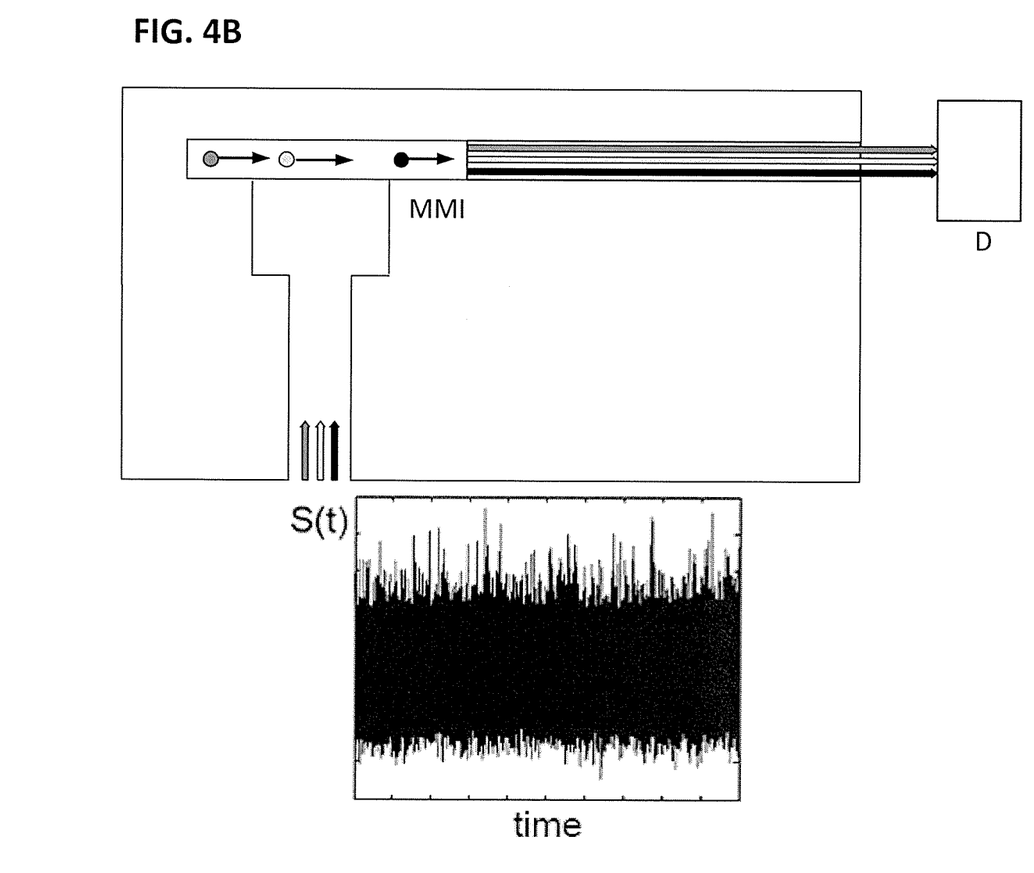
FIG. 4b depicts (top) the proposed on-chip implementation and (bottom) simulated noisy signal from 30 fluorescent particles (10 at each excitation wavelength).
Figure 4C:
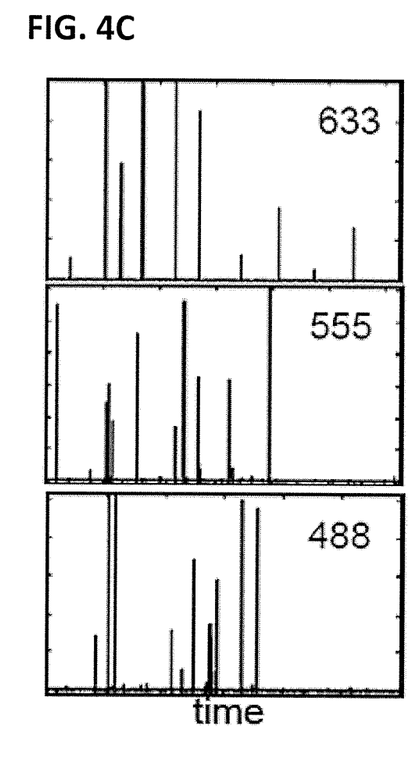
FIG. 4c shows error-free retrieval of particle signals using eq. (1).

FIG. 4b shows the chip layout and another simulation of particles labeled with these dyes in the same channel. Again, despite a noisy background, the individual particles can be retrieved error-free from a single detector signal (FIG. 4c). Thus, spectral multiplexing is accomplished by mapping different wavelengths onto distinct spatial excitation patterns.

Combinatorial Multiplexing Via Multi-Channel, Multi-Wavelength Excitation

Figure 5A:
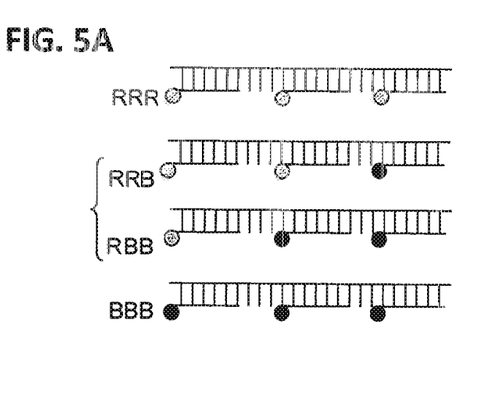
FIG. 5a depicts spectral coding with 3 beacons in 2 colors.

Each of the techniques introduced above is capable of substantial multiplexing. However, the full potential of the MMI-based interferometric approach will be reached if the combinatorial power of spatial and spectral multiplexing is exploited. This aspect is further enhanced by the ability to label nucleic acids with multiple beacons at different colors. FIG. 5a shows the example of beacons with two different fluorophores (R,B) bound to three locations of a nucleic acid target. This will lead to three distinguishable color combinations (four, if it is possible to distinguish RRB and RBB by relative intensities).

Figure 5B:
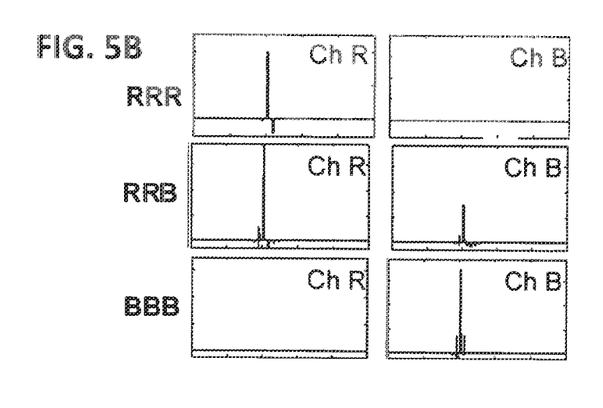
FIG. 5b depicts calculated, error-free identification labeled with different color combinations.
Figure 5C:
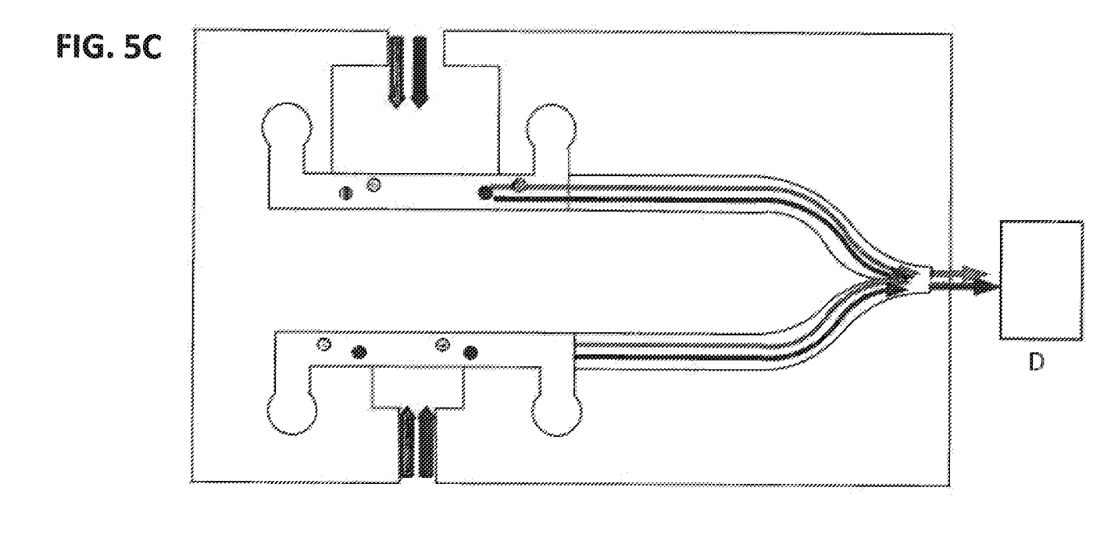
FIG. 5c depicts possible on-chip implementation.

FIG. 5b shows the identification of different color combinations from a single detector signal, obtained using the spectral multiplex method. Note that particles with multiple labels are identified by the coincidence (by a small, predictable shift) of particles in adjacent "color channels" (Ch R,B with $\Delta t_R$ and $\Delta t_B$).

REFERENCES

The following references are cited in the foregoing written description:

[1] Sanders, G. H. W., Manz, A., "Chip-based microsystems for genomic and proteomic analysis", Trends in Anal. Chem. 19, 364-378 (2000).
[2] Heller, M. J., "DNA microarray technology: Devices, systems, and applications", Ann. Rev. Biomed. Eng. 4, 129-153 (2002).
[3] Chamberlain J. S., Gibbs R. A., Ranier J. E., Nguyen P. N., Caskey C. T., "Deletion screening of the Duchenne muscular dystrophy locus via multiplex DNA amplification", Nucleic Acids Research 16, 11141-11156 (1988).
[4] Hayden M. J., Nguyen T. M., Waterman A., Chalmers K. J., "Multiplex-ready PCR: a new method for multiplexed SSR and SNP genotyping", BMC Genomics 9, 80 (2008).

[5] MacBeath, G., and Schreiber, S. L., "Printing Proteins as Microarrays for High-Throughput Function Determination", Science 289, 1760-1763 (2000).

[6] Stoevesandt, O., Taussig, M. J., and He, M., "Protein microarrays: high-throughput tools for proteomics", Expert Rev Proteomics 6, 145-57 (2009).

[7] Rabkin, C. S., Schulz, T. F., Whitby, D., Lennette, E. T., Magpantay, L. I., Chatlynne, L., and Biggar, R. J., "Interassay correlation of human herpesvirus 8 serologic tests", J. Infect. Dis. 178, 304-309 (1998).

[8] Ling, M. M., Ricks, C., Lea, P., "Multiplexing molecular diagnostics and immunoassays using emerging microarray technologies", Expert Rev. Mol. Diagnostics 7, 87-98 (2007).

[9] PharmaVitae, "Molecular Diagnostics: a primer on an emerging sector", Datamonitor, reference code DMHC2430, November 2008.

[10] Watzinger, F., Ebner, K., and Lion, T., "Detection and monitoring of virus infections by real-time PCR", Mol. Aspects of Medicine 27, 254-298 (2006).

[11] Nitsche, A., Steuer, N., Schmidt, C. A., Landt, O., and Siegert, W., "Different real-time PCR formats compared for the quantitative detection of human cytomegalovirus DNA", Clin. Chem. 45, 1932-1937 (1999).

[12] Vasioukhin, V., Anker, P., Maurice, P., Lyautey, J., Lederrey, C., and Stroun, M., "Point mutations of the N-ras gene in the blood plasma DNA of patients with myelodysplastic syndrome or acute myelogenous leukaemia", Br. J. Haematol. 86, 774-779 (1994).

[13] Anker, P., Lefort, F., Vasioukhin, V., Lyautey, J., Lederrey, C., Chen, X., Stroun, M., Mulcahy, H., and Farthing, M. J. G., "K-ras mtuations are found in DNA extracted from the plasma of patients with colorectal cancer", Gastroenterology 112, 1114-1120 (1997).

[14] Swarup, V., and Rajeswari, M. R., "Circulating (Cell-free) nucleic acids—a promising, non-invasive tool for early detection of several human cancers", WEBS Letters 581, 795-799 (2007).

[15] Fleischhacker, M., and Schmidt, B., "Circulating nucleic acids (CNAs) and cancer—a survey", Biochim. Biophys. Acta 1775, 181-232 (2007).

[16] Chimnqgi, M., Moutureau, S., Pernet, P., Conti, M., Barbu, V., Lemant, J., Sacko, M., Vaubourdolle, M., and Loric, S., "Specific real-time PCR vs. fluorescent dyes for serum-free DNA quantification", Clin. Chem. Lab. Med. 45, 993-995 (2007).

[17] Piatak, M., Saag, M. S., Yang, L. C., Clark, S. J., Kappes, J. C., Luk, K. C., Hahn, B. H., Shaw, G. M., and Lifson, J. D., "High levels of HIV-1 in plasma during all stages of infection determined by competitive PCR", Science 259, 1749-1754 (1993).

[18] Inoue, K., Sugiyama, H., Ogawa, H., Nakagawa, M., Yamagami, T., Miwa, H., Kita, L., Hiraoka, A., Masaoka, T., Nasu, K., Kyo, T., Dohy, H., Nakauchi, H., Ishidate, T., Akiyama, T., and Kishimoto, T., "WT1 as a new prognostic factor and a new marker for the detection of minimal residual disease in acute leukemia", Blood 84, 3071-3079 (1994).

[19] Taberlet, P., Griffin, S., Goossens, B., Questiau, S., Manceau, V., Escaravage, N., Waits, L. P., Bouvet, J., "Reliable genotyping of samples with very low DNA quantities using PCR", Nucl. Acids Res. 24, 3189-3194 (1996).

[20] Lagally, E. T., Emrich, C. A., and Mathies, R. A., "Fully integrated PCR-capillary electrophoresis microsystem for DNA analysis" Lab Chip 1, 102-107 (2001).

[21] Liu, P., Li, X., Greenspoon, S. A., Scherer, J. R., and Mathies, R. A., "Integrated DNA purification, PCR, sample cleanup, and capillary electrophoresis microchip for forensic human identification", Lab Chip 11, 1041-1048 (2011).

[22] Chiu, C. Y., Alizadeh, A. A., Rouskin, S., et al., "Diagnosis of a critical respiratory illness caused by human metapneumovirus by use of a pan-virus microarray", J Clin Microbiol. 45, 2340-2343 (2007).

[23] Chiu, C. Y., Rouskin, S., Koshy, A., et al., "Microarray detection of human parainfluenzavirus 4 infection associated with respiratory failure in an immunocompetent adult", Clin Infect Dis. 43, e71-76 (2006).

[24] Tang, P., and Chiu, C., "Metagenomics for the discovery of novel human viruses", Future Microbiol. 5, 177-189 (2010).

[25] D. Yin, J. P. Barber, A. R. Hawkins, D. W. Deamer, and H. Schmidt, "Integrated optical waveguides with liquid cores", Applied Physics Letters 85, 3477 (2004).

[26] Schmidt, H., and Hawkins, A. R., "Optofluidic waveguides: I. Concepts and implementations", Microfluidics and Nanofluidics 4, 3-16 (2008).

[27] Hawkins, A. R., and Schmidt, H., "Optofluidic waveguides: II. Fabrication and structures," Invited review, Microfluidics and Nanofluidics 4, 17-32 (2008).

[28] Barber, J. P., Conkey, D. B., Lee, J. R., Hubbard, N. B., Howell, L. L., Yin, D., Schmidt, H., and Hawkins, A. R., "Fabrication of Hollow Waveguides with Sacrificial Aluminum Cores", IEEE Photonics Technology Letters 17, 363 (2005).

[29] Barber, J. P., Lunt, E., George, Z., Yin, D., Schmidt, H., and Hawkins, A. R., "Integrated Hollow Waveguides with Arch-shaped Cores", IEEE Photonics Technology Letters 18, 28 (2006).

[30] Hubbard, N. B., Howell, L. L., Barber, J. P., Conkey, D. B., Hawkins, A. R., and Schmidt, H., "Mechanical models and design rules for on-chip micro-channels with sacrificial cores", Journal of Micromechanics and Microengineering 15, 720, (2005).

[31] Lunt, E. J., Measor, P., Phillips, B. S., Kühn, S., Schmidt, H., and Hawkins, A. R., "Improving solid to hollow core transmission for integrated ARROW waveguides", Optics Express 16, 20981-20986 (2008).

[32] Lunt, E. J., Wu, B., Keeley, J. M., Measor, P., Schmidt, H., and Hawkins, A. R., "Improving Hollow ARROW Waveguides on Self-Aligned Pedestals for Improved Geometry and Transmission", IEEE Phot. Tech. Lett. 22, 1041 (2010).

[33] Zhao, Y., Jenkins, M., Measor, P., Leake, K., Liu, S., Schmidt, H., and Hawkins, A. R., "Hollow Waveguides with Low Intrinsic Photoluminescence Fabricated with Ta2O5 and SiO2 Films," Applied Physics Letters 98, 091104 (2011).

[34] Yin, D., Barber, J. P., Hawkins, A. R., and Schmidt, H., "Highly efficient fluorescence detection in picoliter volume liquid-core waveguides", Appl. Phys. Lett. 87, 211111 (2005).

[35] Yin, D., Lunt, E. J., Barman, A., Hawkins, A. R., and Schmidt, H., "Microphotonic control of single molecule fluorescence correlation spectroscopy using planar optofluidics", Optics Express 15, 7290-7295 (2007).

[36] Yin, D., Barber, J. P., Deamer, D. W., Hawkins, A. R., and Schmidt, H., "Single-molecule detection sensitivity using planar integrated optics on a chip", Opt. Lett. 31, 2136 (2006).

[37] S. Kühn, P. Measor, E. J. Lunt, B. S. Phillips, D. W. Deamer, A. R. Hawkins, and H. Schmidt, "Loss-based optical trap for on-chip particle analysis", Lab on Chip 9, 2212 (2009).

[38] P. Measor, S. Kühn, E. J. Lunt, B. S. Philips, A. R. Hawkins, and H. Schmidt, "Multi-mode mitigation in an optofluidic chip for particle manipulation and sensing", Optics Express 17, 24342 (2009),

[39] A. Chen, M. M. Eberle, E. J. Lunt, S. Liu, K. Leake, M. I. Rudenko, A. R. Hawkins, and H. Schmidt, "Dual-color fluorescence cross-correlation spectroscopy on a planar optofluidic chip," Lab on Chip 11, 1502-1506 (2011).

[40] Yin, D., Lunt, E. J., Rudenko, M. I., Deamer, D. W., Hawkins, A. R., and Schmidt, H., "Planar optofluidic chip for single particle detection, manipulation, and analysis", Lab Chip 7, 1171-1175 (2007).

[41] Rudenko, Mi., Kühn, S., Lunt, E. J., Deamer, D. W., Hawkins, A. R., and Schmidt, H., "Ultrasensitive Qβ Phage Analysis Using Fluorescence Correlation Spectroscopy on an Optofluidic Chip", Biosensors and Bioelectronics 24, 3258-3263 (2009).

[42] Tyagi, S. and Kramer, F. R., "Molecular beacons: probes that fluoresce upon hybridization," Nature Biotechnol. 14, 303-308 (1996).

[43] Drake, T., and Tan, W., "Molecular beacon DNA probes and their bioanalytical applications," Applied Spectroscopy 58, 269-280 (2004).

[44] Bonnet, G., Tyagi, S., Libchaber, A., and Kramer, F. R., "Thermodynamic basis of the enhanced specificity of structured DNA probes", PNAS 96, 6171-6176 (1999).

[45] Sinseimer, D., Leekha, S., Park, S., Marras, S., Koreen, L., Willey, B., Naidich, S., Musser, K., and Kreiswirth, B. N., "Use of a multiplex molecular beacon platform for rapid detection of methicillin and vancomycin resistance in *staphylococcus aureus*", J. Clinical Microbiology 43, 4585-4591 (2005).

[46] Soldano, L. B., and Pennings, E. C. M., "Optical multimode interference devices based on self-imaging: Principles and applications", J. Lightw. Tech. 13, 615-627 (1995).

[47] Li, B., Chua, S., Leitz, C., and Fitzgerald, E. A., "1×2 optical waveguide filters based on multimode interference for 1.3 and 1.55 mm operation", Opt. Eng. 41, 723-727 (2002).

[48] Khalil, D., and Yehia, A., "Two-dimensional multimode interference in integrated optical structures", J. Opt. A. 6, 137-145 (2004).

[49] Lien, V., Zhao, K., Berdichevsky, Y., and Lo, Y., "High sensitivity cytometric detection using fluidic-photonic integrated circuits with array waveguides", IREE J. Sel. Top. Qu. Elec. 11, 827-834 (2005).

[50] Chen, C., Tsai, F., Lien, V., Justis, N., and Lo, Y., "Scattering-based cytometric detection using integrated arrayed waveguides with microfluidics", IEEE Phot. Tech. Lett. 19, 441-443 (2007).

[51] Godin, J., Chen, C., Cho, S. H., Qiao, W., Tsai, F., and Lo, Y., "Microfluidics and photonics for bio-system-on-a-chip: A review of advancements in technology towards a microfluidic flow cytometry chip", J. Biophoton. 1, 355-376 (2008).

We claim:

1. A method for using spatially distributed interferometric excitation in an optical diagnostic instrument, comprising:
    using a multi-mode interferometer (MMI) to create a wavelength dependent excitation pattern in a fluidic channel in direct contact with the MMI, wherein the excitation pattern includes a wavelength-dependent number, k, of light spots in the fluidic channel;
    causing a fluorescent or light scattering particle to flow in the channel past the MMI and the entire excitation pattern so as to produce k fluorescence or light scattering pulses at time steps Δt, wherein Δt depends on the spacing of the light spots in the fluidic channel;
    detecting the k fluorescence or light scattering pulses and producing a measured detector signal S(t); and
    identifying the fluorescent or light scattering particle based on a predefined algorithm and the measured detector signal S(t).

2. A method as recited in claim 1, wherein the MMI comprises an optical waveguide supporting N waveguide modes that propagate in the optical waveguide with different wave vectors and wherein the N modes comprise electric fields that interfere to create k well-defined spots spaced by w/k at lengths $L_k = 3L_\pi/(4k)$, where $L_\pi$ is a characteristic length that depends on the MMI width w and scales inversely with wavelength λ.

3. A method as recited in claim 1, wherein the predefined algorithm comprises creating a new signal F(t) from the measured detector signal S(t) in the following way: $F(t)=S(t)*S(t-\Delta t)* \ldots *S(t-(k-1)*\Delta t)$ where Δt is the time it takes for the fluorescent or scattering particle to move from one of the excitation spots to the next.

4. A method as recited in claim 1, wherein spatial multiplexing is achieved by exciting a plurality of multi-mode interferometers in parallel.

5. A method as recited in claim 4, wherein at least first and second multi-mode interferometers are employed to excite first and second channels, respectively, wherein each channel is excited with an MMI using the same wavelength but different MMI dimensions corresponding to different numbers of excitation spots such that particles flowing through the different channels produce fluorescence peaks at distinct time intervals.

6. A method as recited in claim 5, wherein a single detector is employed to detect and record fluorescence pulses generated in the first and second channels, and particle detection and assignment to a channel of origin is accomplished using the predefined algorithm.

7. A method as recited in claim 1, wherein spectral multiplexing is achieved by exciting the MMI with first and second excitation light colors, thereby producing different spot spacings and, thus, different correlation times Δt(λ).

8. A method as recited in claim 7, wherein the dimensions, including width (w) and length (L) of the MMI coincide with excitation wavelengths of selected dyes.

9. A method as recited in claim 8, wherein the MMI width, w, is approximately 50 μm and the MMI length, L, is approximately 875 μm, producing a predetermined number of spots for excitation of dyes Alexa 488, Alexa 555, and Alexa 647, respectively.

10. A method as recited in claim 9, wherein multiple fluorescent particles are marked with said dyes, and a single detector is employed to detect and record fluorescence pulses generated in a single channel.

11. A method as recited in claim 1, wherein a combination of spatial and spectral multiplexing is performed.

12. A method as recited in claim 11, wherein spatial multiplexing is achieved by exciting a plurality of MMIs in parallel, and spectral multiplexing is achieved by exciting a single MMI with a plurality of excitation light colors.

13. A method as recited in claim 12, wherein nucleic acid particles are labeled with multiple beacons, or fluorophores, of different colors, at multiple locations of each nucleic acid particle; and wherein different color combinations are detected using a single detector signal.

14. An instrument, comprising:
a fluidic channel;
a multi-mode interferometer (MMI) configured to create a wavelength dependent excitation pattern in the fluidic channel, wherein the fluidic channel is in direct contact with the MMI, wherein the MMI comprises an optical waveguide supporting N waveguide modes that propagate in the optical waveguide with different wave vectors and wherein the N modes comprise electric fields that interfere to create varying field patterns with k well-defined spots spaced by w/k at lengths $L_k=3L_\pi/(4k)$, where $L_\pi$ is a characteristic length that depends on the MMI width w and scales inversely with wavelength $\lambda$;
a port configured for injecting a fluorescent or light-scattering particle into the fluidic channel so as to flow past the MMI and the entire excitation pattern and produce k fluorescence pulses at time steps $\Delta t$, wherein $\Delta t$ depends on the spacing of the light spots in the fluidic channel;
an optical waveguide configured with respect to the fluidic channel for guiding the k fluorescence or light scattering pulses; and
an optical detector for detecting the k fluorescence or light scattering pulses;
wherein the fluorescent or light scattering particle is identifiable based on a predefined algorithm.

15. An instrument as recited in claim 14, comprising first and second multi-mode interferometers configured to excite first and second fluidic channels, respectively, wherein each fluidic channel is excited with an MMI using the same wavelength but different MMI dimensions corresponding to different numbers of excitation spots such that particles flowing through the different fluidic channels produce fluorescence or light scattering peaks at distinct time intervals.

16. An instrument as recited in claim 15, wherein the optical detector is configured to detect and record fluorescence or light scattering pulses generated in the first and second fluidic channels, and particle detection and assignment to a channel of origin is accomplished using the predefined algorithm.

17. An instrument as recited in claim 14, wherein the dimensions (w, L) of the MMI coincide with excitation wavelengths of selected dyes.

* * * * *